United States Patent [19]

Grgic et al.

[11] Patent Number: 4,565,085

[45] Date of Patent: Jan. 21, 1986

[54] METHOD OF AND APPARATUS FOR MEASURING THE DEGREE OF GAS CHARGE IN A LIQUID SYNTHETIC RESIN COMPONENT

[75] Inventors: Ivica Grgic, Munich; Wolfgang Söchtig, Germering, both of Fed. Rep. of Germany

[73] Assignee: Krauss-Maffei Aktiengesellschaft, Munich, Fed. Rep. of Germany

[21] Appl. No.: 610,244

[22] Filed: May 14, 1984

[30] Foreign Application Priority Data

May 13, 1983 [DE]  Fed. Rep. of Germany ....... 3317486
Oct. 4, 1983 [DE]  Fed. Rep. of Germany ....... 3336037

[51] Int. Cl.⁴ .......................... G01N 9/26; G01N 7/00
[52] U.S. Cl. ......................................... 73/19; 73/438; 137/91
[58] Field of Search ................... 73/19, 433, 434, 438, 73/439; 137/3, 88, 91; 264/40.1, 50

[56] References Cited

U.S. PATENT DOCUMENTS

| | | | |
|---|---|---|---|
| 2,541,102 | 2/1951 | Rymal | 73/438 |
| 3,690,184 | 9/1972 | Chadenson | 73/438 |
| 4,089,206 | 5/1978 | Raffel et al. | 73/19 |
| 4,195,527 | 4/1980 | Ebeling | 73/434 |
| 4,201,082 | 5/1980 | Dockhorn | 73/438 |
| 4,365,505 | 12/1982 | Holzl | 73/19 |

*Primary Examiner*—S. Clement Swisher
*Attorney, Agent, or Firm*—Karl F. Ross; Herbert Dubno

[57] ABSTRACT

A method of and apparatus for the measurement of the degree of charging of a liquid synthetic resin component with a gas in which the flushing of the measuring column and the detection of the hydrostatic pressure are effected solely by control of the intake valve to the measuring chamber, a discharge valve at the bottom of an overflow chamber connected to the measuring chamber, and a three position valve connected to the top of the overflow chamber. In one position of this latter valve, a pressurized gas is applied to the overflow chamber to drive overflow liquid component back to the tank: in another position of this valve the column can be equilibrated with atmospheric pressure: in a third position this valve is closed.

5 Claims, 1 Drawing Figure

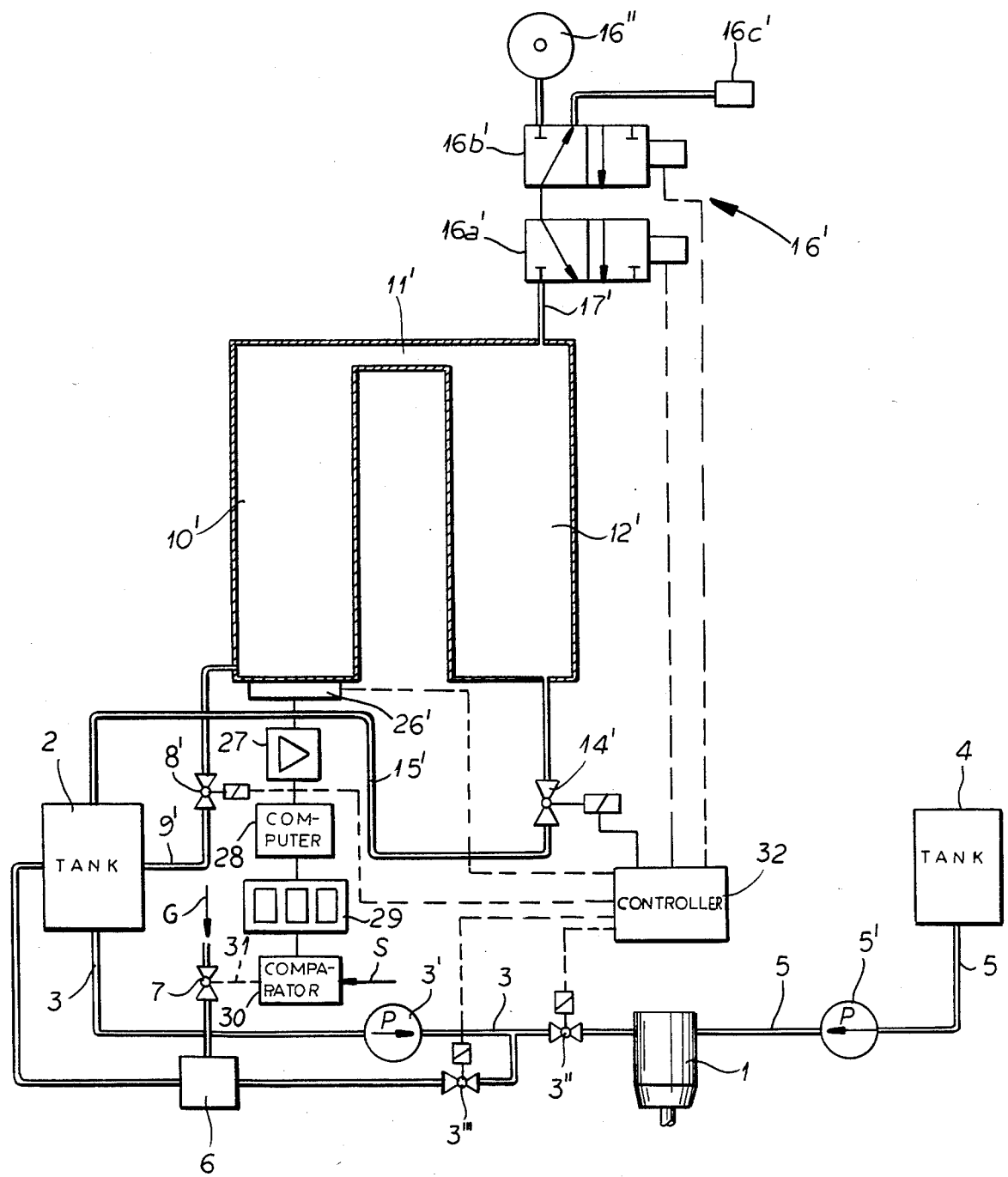

METHOD OF AND APPARATUS FOR MEASURING THE DEGREE OF GAS CHARGE IN A LIQUID SYNTHETIC RESIN COMPONENT

CROSS REFERENCE TO RELATED APPLICATIONS

This application is related to the commonly assigned copending application Ser. No. 610,017 filed May 14, 1984 in the name of Emil Hölzl and based upon German Application No. P 33 17 486.5 filed May 13, 1983. This application is based upon an addition to the latter application filed in the German Patent Office under the No. 33 36 037.5 filed Oct. 4, 1983.

FIELD OF THE INVENTION

Our present invention relates to a method of determining the gas content of a liquid synthetic resin component which can be utilized to form a foamed synthetic resin composition. More particularly, this invention relates to a method of measuring this parameter or an equivalent parameter in the form of the absolute density of a gas-charged liquid synthetic resin component, and to an apparatus for carrying out the improved method.

BACKGROUND OF THE INVENTION

In the production of foamed synthetic resin materials, e.g. foamed polyurethane, it is a common practice to incorporate, as a foaming agent, a gas under pressure into one of the liquid components which are to be mixed to form the reactive system discharged into a mold.

As is pointed out in the aforementioned application which is incorporated entirely herein by reference, it is important for the quality of the foamed products which are produced to maintain the gas content of the gas-charged liquid component substantially constant. For this it has been necessary to sample the gas-charged liquid component in its tank, and to carry out a series of determinations which are onerous and higly imprecise if prior art techniques are utilized.

The Hölzl Application

In the Hölzl application, which has not yet entered into the prior art, there is disclosed an improved method of determining the gas content of a liquid synthetic resin component for a foamed synthetic resin, namely, a gas-charged polyol, in which the liquid is introduced into a measuring vessel to form a column of a fixed height h as determined by an overflow at an upper portion of this column. The hydrostatic pressure p of the column can then be determined and the absolute density of the gas-charged liquid, represented as $\rho$ in accordance with the relationship $\rho = (p/h \cdot g)$ in which g is the acceleration of gravity and h is also a constant of the overflow arrangement. The absolute density is, of course, a function of the gas content of the liquid component and, indeed, knowing the characteristics of the liquid component, such as its density before the gas charged thereof, it is possible to determine the gas content by simple calculation.

That application also discloses a novel apparatus for carrying out the measurements, utilizing computer calculation of the gas proportion and control of the charging unit. In that apparatus, however, a fairly complex system was required to handle the overflow.

OBJECTS OF THE INVENTION

It is the principal object of the present invention to provide a method of and an apparatus for the measurement of the degree of charging of a liquid synthetic resin component with a gas and which represents improvements upon the system described in the aforementioned application while extending the principles thereof.

Yet another object of the invention is to provide an improved method which represents a simplification of the approach utilized in the aforementioned application and which can result in a reduction in the apparatus cost as well.

SUMMARY OF THE INVENTION

We have now found that it is possible to simplify this system described in the abovementioned application and eliminate the piston system there utilized for handling the overflow and effecting flushing of the measurement vessel or cylinder, and the relatively complex control system for that piston, if the closed overflow vessel connected to the overflow of the measuring vessel is provided at a lower portion thereof with a controllable discharge valve while at its upper portion a controllable switching valve is provided.

According to the present invention, this switching valve has a first position in which the upper port is closed, a second position in which the interior of the overflow vessel through the upper port is connected to a pressure source, e.g. a compressed air source, and a third position in which this upper port is vented to the atmosphere.

In the method of operating this system, for flushing of the measuring vessel, the intake valve and the discharge valve are opened and the upper port is closed. The liquid component can the flow from the tank into the measuring vessel and can overflow freely into the overflow vessel, the intake valve can then be closed and the switching valve opened to supply compressed air or some other pressure gas to this overflow vessel. The switching valve can then be closed and the intake valve opened and the action repeated until the desired degree of flushing has occurred and the measuring vessel is filled to overflowing with the fresh sample of the liquid component.

The hydrostatic pressure measurement is then taken after the intake valve and the discharge valve are closed and the switching valve has been opened to apply atmospheric pressure at the head of the column.

BRIEF DESCRIPTION OF THE INVENTION

The above and other objects, features and advantages of the present invention will become more readily apparent from the following description reference being made to the accompanying drawing in which the sole FIGURE is a vertical section through a measuring apparatus embodying the invention with portions illustrated in flow diagram and other portions illustrated in block or circuit diagram form.

SPECIFIC DESCRIPTION

In the drawing we show an apparatus similar to that described and illustrated in the above mentioned copending application but different therefrom with respect to the overflow cylinder and its controller. To the extent not otherwise described herein, therefore, the system of this application can be considered to operate identically to that of the abovementioned application which is hereby incorporated by reference as noted.

The apparatus shown in the drawing comprises a mixing head which can open into a mold for the production of foamed polyurethane articles and can be of the recirculating type if desired wherein the two components are separated from one another and recycled to the respective tanks if recirculation is desired, but in which the two components intimately mix and in their interreactive form are discharged into the mold.

Diisocyanate component is fed from a tank 4 via a line 5 and a pump 5' to the head 1 whereas the polyol component is fed from the tank 2 via a line 3 and a pump 3' to the head 1. Along the line 3, a valve 3" is provided and between the pump 3' and the valve 3", a pump branch including the valve 3'" runs to a pressurization unit 6 and from the latter unit to the tank 2.

The supply of the charged gas going to this unit 6 is controlled by a valve 7.

In practice, the valve 7 may be regulated by a comparator 30 receiving a set point value S representing the desired level of gas in the polyol liquid component and an actual value signal which derives from the measurement of the hydrostatic pressure to be described.

When the valve 3" is closed and the valve 3'" is opened, the pump 3' can recirculate the polyol liquid component from the tank 2 through the gas-charging unit 6 and back to the tank 2.

A measuring vessel 10' is connected by a feed line 9' having an intake valve 8' to the polyol tank 2.

The measuring vessel 10' is provided at its bottom end with a pressure sensor 26' which can be a bourdon gauge, a piezoelectric pressure sensor or a strain gauge pressure sensor.

The upper end of the vessel 10' is provided with an overflow 11' opening into an overflow vessel 12' which is closed and, in the present case, of a constant volume.

At its low end, the overflow vessel 12' is provided with an outlet pipe 15' returning the overflow component to the tank 2 and equipped with a discharge valve 14'.

At an upper port 17' at the upper end of the overflow vessel 12', the latter is equipped with a switching valve assembly 16' which can, in the preferred embodiment consist of a two-port, two-position valve 16a' (2/2 valve) and a three-port, two-position valve 16b' (3/2 valve). The latter has one port connected to a pressurized gas source, e.g. a source 16" of compressed air or of the same gas as was used to charge the liquid component. Another port is connected to a muffler 16c' opening to the atmosphere.

The pressure sensor 26' is connected to an amplifier 27 which supplies its output to a computer 28, the latter feeding a display or indicator 29 for displaying the parameter. The parameter is also supplied as an actual value measurement to the comparator 30.

A controller 32 is connected to the valves 16a', 16b', 3", 3'", 8', 14' for sequencing the apparatus to carry out the successive measurements and this computer may be of the microprocessor preprogrammed type. The computer 28 may be preprogrammed with the empirical data relating to the nature and composition of the liquid component and through gas to provide the display of the gas content directly, or may be designed to simply carry out the mathematical calculations required for the determination of the desired parameter from the measured pressure value and the data relating to the height h, etc.

The sequencing circuit 32 thus effects a measurement sequence as follows:

For each sample, the measuring vessel 10' is first flushed with the liquid component from the tank 2 by opening the discharge valve 14' and the intake valve 8' and closing the switching valves 16. The latter component flows from the liquid into the measuring vessel 10' through the overflow 11' and into the overflow tank 12'. It is returned from the overflow vessel 12' to the tank.

After flushing is complete, the liquid component is discharged from the overflow tank through this open valve 14' by closing valve 8' and connecting the pressurized gas source 16" with the overflow vessel 12.

For the measurement step which then follows, the intake valve 8' and the discharge valve 14' are closed and the vessel 12' is vented to the atmosphere by the valve 16' to apply atmospheric pressure to the head of the column. After an expansion phase, the pressure sensor 26' is enabled by the controller 32 to provide a reading which can be displayed directly as the absolute density or as the degree of charging of the liquid component with gas; the measurement is of course the measurement at atmospheric pressure.

We claim:

1. In an apparatus for the determination of a parameter representing the gas content of a gas-charged liquid synthetic resin component such as a synthetic resin component utilized in the production of foamed synthetic resins, wherein a sample of the gas charged liquid component is introduced into an upright measuring vessel, is caused to overflow at an overflow to the tip of said vessel, and the hydrostatic pressure of the resulting column of the gas charged liquid component is measured and, from the measurement of the hydrostatic pressure, the parameter is determined, the improvement which comprises:

a closed overflow vessel connected to said overflow of said measuring vessel;

a feed line provided with an intake valve connected with said measuring vessel for delivering said gas charged liquid component to a measuring vessel from said tank;

a discharge valve connecting said overflow vessel to a point below said overflow with said tank for returning overflow liquid component to said tank, said overflow vessel having a port to an upper portion thereof;

a switching valve connected to said port and having a first position connecting said port to a source of pressurized gas for driving overflow liquid component from said overflow vessel to said tank, a second position for venting said vessels to the atmosphere to apply atmospheric pressure to the top of said column, and a third position wherein said port is blocked; and means for operating said valves in a predetermined relationship to effect flushing of said liquid component through said measuring vessel, discharge of overflow liquid component from said overflow vessel, and equilibrating the top of said column with atmospheric pressure solely by an operation of said valves.

2. The improvement defined in claim 1 wherein said tank is provided with a pump, a gas charging unit, and valves controllable to divert pumped liquid component through said unit and back into said tank for charging of said liquid component with said gas.

3. The improvement defined in claim 2 wherein said measuring vessel is provided at its bottom with a sensing means for said hydrostatic pressure, said sensing means being connected to an amplifier and to a computer for calculating said parameter, said computer having a display for displaying said parameter.

4. The improvement as defined in claim 3 wherein said parameter is fed as an actual value measurement to a comparator having a set point value representing the desired degree of gas charging of said liquid component, a gas control valve being connected with said unit and responsive to said computer for maintaining the degree of charging of said liquid component with gas substantially constant.

5. In a method of determining a parameter representing the degree of charging of a gas-charged liquid synthetic resin component with a charging gas for the production of a foamed synthetic resin wherein the gas charged liquid component is admitted to an upright measuring vessel and permitted to overflow to an upper end thereof to establish a column of fixed height in said measuring vessel, and the hydrostatic pressure of said column is measured to generate said parameter, the improvement which comprises the steps of:

collecting overflow liquid component in a closed overflow vessel communicating with said measuring vessl with an overflow at an upper end thereof;

flushing said liquid component through said vessels by opening an intake valve connecting said measuring vessel with a tank for said liquid component and a discharge valve connecting said overflow vessel with said tank;

with said discharge valve opened, connecting an upper end of said overflow vessel with a source of pressurized gas to drive overflow liquid component from said overflow vessel into said tank;

with said intake valve and discharge valve closed, communicating said overflow vessel with the atmosphere to apply atmospheric pressure at the top of said column; and effecting said measuring after the application of said atmospheric pressure to the top of said column.

* * * * *